United States Patent [19]

Fenimore

[11] 4,248,904

[45] Feb. 3, 1981

[54] METHOD FOR PREPARING SAMPLES FOR APPLICATION TO A THIN LAYER CHROMATOGRAPHIC SHEET

[76] Inventor: David C. Fenimore, 1300 Moursund, Houston, Tex. 77030

[21] Appl. No.: 39,960

[22] Filed: May 21, 1979

Related U.S. Application Data

[63] Continuation-in-part of Ser. No. 909,207, May 25, 1978, abandoned.

[51] Int. Cl.³ .............................................. B05D 3/00
[52] U.S. Cl. ........................................ 427/2; 210/658; 422/58; 427/275; 427/294
[58] Field of Search ................... 118/44, 200, 205, 50; 427/2, 445, 265, 269, 275, 294; 422/58; 210/198 C, 31 C; 195/103.5 M, 101, 127; 425/388

[56] References Cited

U.S. PATENT DOCUMENTS

| | | | |
|---|---|---|---|
| 2,066,130 | 12/1936 | Von Hofe et al. | 118/205 |
| 2,124,711 | 7/1938 | Rowell | 101/41 |
| 2,284,491 | 5/1942 | Mandell | 91/47 |
| 2,647,337 | 8/1953 | Martin | 41/1 |
| 3,757,952 | 9/1973 | Baitsholts et al. | 210/198 C |
| 3,868,901 | 3/1975 | Valiela | 101/41 |
| 3,871,293 | 3/1975 | Valiela | 101/41 |
| 4,011,350 | 3/1977 | Markovits et al. | 427/2 |

FOREIGN PATENT DOCUMENTS

| | | |
|---|---|---|
| 424226 | 8/1911 | France . |
| 461244 | 2/1937 | United Kingdom . |
| 472796 | 9/1937 | United Kingdom . |
| 1161534 | 8/1969 | United Kingdom . |

*Primary Examiner*—Shrive P. Beck
*Attorney, Agent, or Firm*—Arnold, White & Durkee

[57] ABSTRACT

A chemically inert, non-absorptive applicator sheet, a depression defined by a recessed portion of the applicator sheet, a transfer coating on at least a portion of a top surface of the applicator sheet, means for evaporating a solution of sample and carrier solvent deposited on the transfer coating, and a displacement mechanism for displacing a sample formed in the recess are disclosed. The depression in the applicator sheet may be formed by imposing a suction beneath the applicator sheet; and a displacement of a sample formed in the depression may be accomplished by introducing pressure beneath the applicator sheet.

9 Claims, 17 Drawing Figures

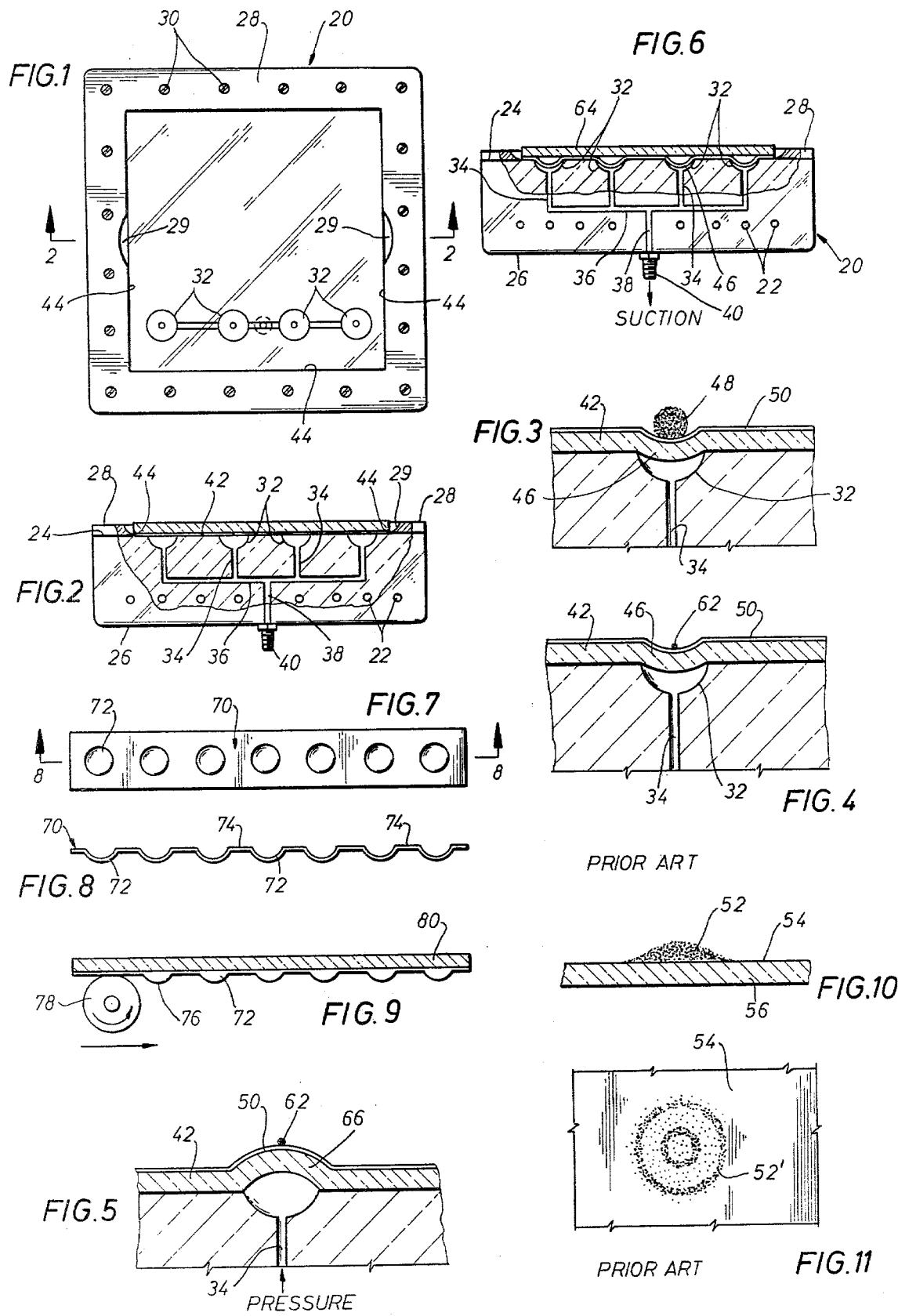

METHOD FOR PREPARING SAMPLES FOR APPLICATION TO A THIN LAYER CHROMATOGRAPHIC SHEET

This application is a continuation-in-part of Ser. No. 909,207, filed May 25, 1978, and now abandoned.

BACKGROUND OF THE INVENTION

This invention relates generally to a novel method and apparatus for preparing test samples for application onto a thin-layer chromatographic plate. More particularly, this invention relates to a method and apparatus for applying extremely small samples to thin-layer chromatography (TLC) plates where the solvent carrying the sample is evaporated prior to a transfer of the sample to the TLC plates.

In the past, it has been common to mix a sample together with a carrier solvent and then apply the mixture of sample and solvent to a TLC plate. The solvent would then be evaporated after application of the mixture. Devices such as syringes with very fine needles or capillary pipettes have been used to apply the sample mixture to TLC plates.

A wide variety of methods and apparatus have been available to enhance evaporation of the solvent from the mixture applied to the TLC plate or sheet. For example, vacuum sources or heaters may be placed in the vicinity of the sample. In any event, in the prior art, evaporation took place on the TLC plate leaving the sample. Typically, the evaporation took place in stages leaving small concentric rings of sample material at the location where the mixture was originally applied with the result that a sample might be present over the entire area where the mixture was originally applied to the TLC plate.

In instances where a very small sample is required, for example, in high-performance thin layer chromatography (HPTLC), greater care is required in applying the sample mixture to the TLC plate. For example, it has been known to use a platinum-iridium capillary pipette countered-balanced in a delicate instrument to provide a sample having diameter in the order of 2 mm. In HPTLC it has been found that a small, highly concentrated sample provides more satisfactory results than a larger, more dispersed sample.

While prior art arrangements have exhibited at least a degree of utility in providing a suitably small sample for HPTLC, room for significant improvement remains. It is believed that extremely small samples may be applied with greater consistency in size. Moreover, with known techniques, a painstaking procedure is required for the preparation of each sample, and it is believed that the speed of application may be significantly improved to facilitate the handling of large numbers of samples, for example, in instances where HPTLC is used to determine the presence of drugs in blood serum. In such instances, large numbers of samples need to be quickly and accurately prepared, preferably simultaneously.

The prior art includes several patent disclosures containing subject matter directed to methods and apparatus for preparing samples or specimens for chromatographic analysis, for example, U.S. Pat. No. 3,266,554, to Brownrigg and U.S. Pat. No. 3,757,952 to Baitsholts, et al.

The Brownrigg patent discloses a method and apparatus whereby syringes attached to tubes are used to deposit a droplet onto absorbent paper. Air is drawn through the absorbent paper to facilitate evaporation of the solvent carrying the sample. The size of the sample is controlled by positioning the tube in relation to the absorbent paper.

The Baitsholts et al. patent discloses a template for applying samples to a chromatographic sheet. A template having apertures which function as "wells" is positioned over a TLC plate. The samples are introduced into the wells which function to prevent spreading of the samples along the chromatographic sheet while the samples dry.

With both of these prior art devices, the evaporation of the solvent takes place on the TLC plate itself, which may result in problems of the type noted above. In addition, it is believed that these prior art devices are not suitable to provide rapid application of large numbers of samples simultaneously.

The problems enumerated in the foregoing are not intended to be exhaustive but rather are among many which tend to impair the effectiveness of previously known methods and apparatus for preparing and applying samples for use in a thin layer chromatography. Other noteworthy problems may also exist; however, those presented above should be sufficient to demonstrate that methods and apparatus appearing in the prior art have not been altogether satisfactory.

OBJECTS AND SUMMARY OF A PREFERRED EMBODIMENT OF THE INVENTION

Recognizing the need for an improved method and apparatus for applying samples to TLC plates, it is, therefore, a general object of the present invention to provide a novel method and apparatus for preparing samples for application to a TLC plate which minimize or reduce the problems of the type previously noted.

It is a more particular object of the present invention to provide a novel method and apparatus for preparing samples for application to a TLC plate which produce a sample having an extremely small area in relation to the droplet of solvent carrying that sample.

It is another object of the present invention to provide a novel method and apparatus for preparing samples for application to a TLC plate which facilitate rapid application of samples.

It is yet another object of the present invention to provide a novel method and apparatus for preparing samples for application to a TLC plate which enable the simultaneous application of a large number of samples.

A method according to a presently preferred embodiment of the invention intended to substantially accomplish the foregoing objects includes the steps of providing a depression on a chemically inert, non-absorptive applicator sheet, preferably coating the depression with a layer of polyfluorinated transfer liquid, introducing a solution of a sample and a solvent into the depression, evaporating the solvent to provide a speck of sample on the transfer liquid, and then transferring the speck to a TLC plate subsequent to the evaporation. Apparatus for preparing samples include a base member having a depression, a suction apparatus to reduce the pressure in the depression, and pressure means to increase the pressure in the depression.

Unlike the conventional means of introducing the sample to a TLC plate or sheet through single or repeated application of solutions followed by evaporation of carrier solvent from the plate after each application, the present invention provides for evaporation of the solvent prior to application onto a TLC plate. The sample material is transferred to a TLC plate as a solid or as a liquid speck or droplet, the cross-section of which is uninfluenced by solvent diffusion in the absorptive layer of the TLC plate.

Concentration of the sample prior to transfer is accomplished by evaporation of the carrier solvent under carefully controlled conditions on a non-absorptive "applicator sheet" such as fluorinated ethylene/propylene polymer ("FEP") or a polyolefin. Transfer to the TLC plate is facilitated by adding a small amount of liquid transfer fluid to the sample solution which will wet the polymer surface but which is immiscible with the sample solvent and will not dissolve the sample itself. Thus when the solvent is evaporated, the solute is suspended on a film of the added transfer liquid. The surface tension of the solute is sufficient to draw the sample into a small droplet or speck as the solvent evaporates.

The base member of the apparatus is operable to carry an FEP applicator sheet. The applicator sheet is positioned over a series of depressions in the base member. Suction may be applied to each of the depressions in the base plate to draw inwardly the applicator sheet. This results in the formation in the applicator sheet of a depression suitable to contain the small amount of liquid transfer fluid sample solution. There may be formed in the bottom of the depression a very small dimple which can serve as receptacle for the sample. After evaporation of the carrier solvent, pressure may be applied to the depression in the base which causes an outward deflection of the zone immediately above the depression which facilitates transfer or the sample from the applicator sheet to the TLC plate.

Examples of the more important features of this invention have thus been summarized rather broadly in order that the detailed description thereof that follows may be better understood, and in order that the contribution to the art may be better appreciated. There are, of course, additional features of the invention that will be described hereinafter and which will also form the subject matter of the claims appended hereto.

BRIEF DESCRIPTION OF THE DRAWINGS

FIG. 1 is a plan view of an apparatus for preparing samples for application to a TLC sheet;

FIG. 2 is a partial-sectional view taken through section lines 2—2 on the apparatus of FIG. 1;

FIG. 3 is a detailed drawing of a depression of the apparatus of FIGS. 1 and 2 wherein suction has been applied to a flexible applicator plate to provide an indentation in which a droplet of solvent and sample has been applied;

FIG. 4 is the apparatus of FIG. 3 wherein evaporation of the sample has resulted in the formation of a speck sample;

FIG. 5 is the apparatus of FIGS. 3 and 4 wherein pressure has been applied to the applicator plate to cause an extension in the applicator plate to elevate the speck sample above the plane of the applicator plate;

FIG. 6 is a front view of the apparatus shown in FIGS. 1 through 5 and wherein a TLC plate has been placed in proximity to the applicator sheet to effect transfer of the sample from the applicator sheet to the TLC plate;

FIG. 7 is a plan view of an alternative embodiment of apparatus of the present invention showing a plastic-like material having molded-in depressions;

FIG. 8 is a partial-sectional view taken through section lines 8—8 on the apparatus of FIG. 7;

FIG. 9 schematically depicts a TLC plate overlying the apparatus of FIGS. 7 and 8 and wherein a roller or like apparatus is pressed against an underside of the depressions to urge the contents thereof into direct contact with the TLC plate;

FIG. 10 is a partial sectional view depicting the method and apparatus of the prior art and showing a droplet of sample solution;

FIG. 11 is a plan view of a sample formed by evaporating the droplet shown in FIG. 10;

Figure 12:
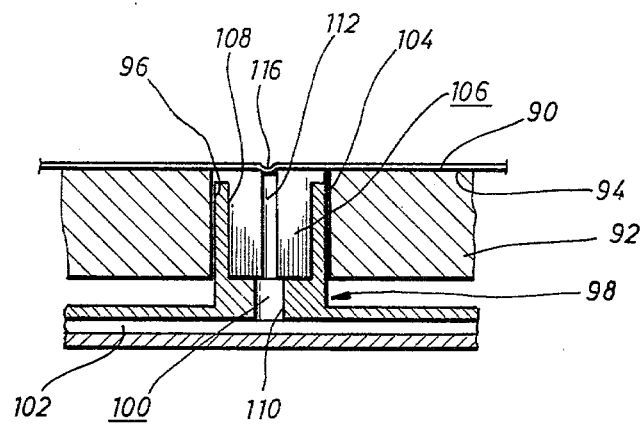
FIG. 12 is a partial-sectional view of an alternative embodiment of the apparatus of the present invention and showing the formation of a dimple prior to the formation of a depression in the applicator sheet.

With reference now to the FIGURES, wherein like reference numerals have been applied to like elements, there is disclosed preferred embodiments of apparatus for preparing samples for application to a TLC plate. With particular reference now to FIGS. 1 and 2, there is shown a base 20. This base 20 is preferably fashioned from acrylic plastic or may be fashioned from any other suitable material demonstrating appropriate strength characteristics and chemical inertness. Electric resistance heating elements 22 may be molded into the base or alternatively channels may be bored to provide conduits for heated fluid for maintaining temperature control of the base 20. In any event, the base has a top side 24 and a bottom side 26. The top side 24 carries a generally rectangular frame 28 preferably fashioned from aluminum and held in place by a series of screws 30 or through other suitable fastening means.

In the top side 24 of the base 20 there are fashioned a plurality of cuplike depressions or control chambers 32. These control chambers may be formed by boring a slight amount into the top side 24 of the base 20. In any event, beneath each control chamber 32 is a control chamber conduit 34 in fluid communication with a manifold 36. The manifold 36 in turn is in fluid communication with a channel 38 terminating on the bottom side 26 of the base 20 at a hose connection 40 or the like.

An applicator sheet 42 is positioned on the top side 24 of the base 20 within the frame. The applicator 42 is preferably approximately 5 mils. in thickness and fashioned preferably from an FEP polymer. It will be appreciated that the applicator sheet 42 may be comprised of materials selected from a range of thicknesses. The thickness of any particular applicator sheet will depend in part upon the material chosen. Materials other than an FEP polymer also would be suitable. For example, polytetrafluoroethylene (sold under a trademark TEFLON) would be a suitable material for the applicator sheet 42. The thickness of an applicator sheet fashioned from TEFLON might be different from that of an FEP polymer. In general, the diameter size and depth of the control chamber 32 may determine the acceptable material and thickness for the applicator sheet 42.

As may be seen in FIGS. 1 and 2, the applicator plate is generally prevented from lateral movement by the inside edges 44 of the frame 28.

Either suction or pressure may be applied to the hose connection 40 by means of known apparatus not here shown. Upon a creation of suction at the hose connection 40, a zone of relatively low pressure is produced in each control chamber 32 with the result that the applicator sheet 42 is urged downwardly toward the control chamber 32 to provide a slight depression 46 as may be seen in FIGS. 3, 4 and 6. It will be appreciated that a slight depression 46 is formed in the applicator sheet 42 at the location of each control chamber 32 upon the creation of a vacuum at the hose connection 40. Each depression 46 is suitable to contain a droplet 48 of a solution of sample material and solvent.

It has been found to be an important element of the present invention that a transfer fluid 50 either be applied to the applicator sheet prior to introduction of the droplet 48 into the depression 46 or mixed together with the droplet 48 prior to introduction of the droplet 48. In any event, the transfer fluid 50 provides a film between the applicator sheet 42 and the droplet 48 to prevent the droplet from coming into direct contact with the applicator sheet. The transfer fluid 50 facilitates formation of the droplet 48 by offering a surface free of resistance to movement of the droplet 48. As a result, the sample solvent draws itself into as small a surface-to-volume ratio as possible, i.e., a sphere.

In the prior art, as shown in FIG. 10, a droplet 52 of sample would be applied directly to a TLC plate 56 and because of the characteristics of a surface 54 thereof, would tend to spread along the surface 54 of the TLC plate 56. With the present invention, the FEP polymer applicator plate 42 with the film of transfer fluid 50, preferably perflurokerosene (PFK), provides a non-wettable surface to the droplet 48, and, hence, the droplet 48 achieves a substantially spherical geometry.

While situated in the depression 46 of the applicator sheet 42, the droplet 48 is subjected to evaporation. Evaporation may be enhanced by heating the base with heating coils 22, heating the environment over the droplet 48, or passing a stream of heated, inert gas over the droplet 48. To enhance evaporation, the base member may be enclosed. This would also serve to prevent dust from coming into contact with the sample material.

In any event, as evaporation takes place, the material within the droplet 48 tends to become more highly concentrated within the depression 46. When substantially all of the solvent has evaporated, a speck sample 62 remains in the depression 46 on a layer of the transfer fluid 50.

The solvent in the droplet 48 is much more highly volatile than the transfer fluid 50, and, hence, the solvent evaporates substantially completely before any significant evaporation of the transfer fluid. Therefore, the transfer fluid is substantially uneffected by the heat and the like which might be utilized to facilitate evaporation of the solvent.

After the solvent has substantially evaporated, a TLC plate 64 may be positioned over the applicator sheet 42 (See FIG. 6). Preferably the TLC plate 64 has the same dimensions as the window formed by the inside surface 44 of the frame 28. Such an arrangement would facilitate the application of a relatively large number of space samples to the TLC plate 64 at a location which enables the TLC plate to be introduced into a predetermined depth of developing liquid.

TLC plates are known in the art; however, it has been found that HPTLC separations may be carried out using 10×10 cm. pre-coated silica gel "60" plates available from E. Merck, Darmstadt, West Germany. It has been found that the apparatus of the present invention is suitable to transfer a sample onto any one of a side variety of known TLC plates commercially available today.

In any event, the TLC plate 64 is positioned over the applicator sheet 42, whereupon the vacuum or negative pressure at the hose connection 40 is relieved, and a slight positive pressure is introduced. The positive pressure at the hose connection 40 causes a positive pressure in the control chamber 32 which results in the extension or urging upward of that portion 66 of the applicator sheet 42 immediately above the control chamber 32 as seen in FIG. 5. This displacement upward may urge the speck sample 62 and transfer fluid 50 against a dry surface of the TLC plate 64 with the result that the speck sample 62 is transferred to the TLC plate 64. The TLC plate 64 is highly adsorbent and draws both the speck sample 62 and the transfer fluid 50 away from the applicator sheet 42 and onto the TLC plate 54. In this manner, the speck sample 62 may be readily transferred in its already reduced size and subsequent to evaporation of the solvent. To facilitate removal of the TLC plate 64 from the window formed by the inside edge 44 of the frame 28, notches 29 are provided. The TLC plate 64 is now ready for subsequent treatment or developing of the sample.

An alternative embodiment of apparatus of the present invention is shown in FIGS. 7 through 9. A strip of plastic-like material such as FEP polymer is fabricated into a sample strip 70 having depressions 72 molded thereinto. A sample may be evaporated in these depressions in a similar manner to that discussed in connection with FIGS. 1 through 6. After evaporation of the solvent has taken place, a TLC plate 80 is placed over the strip 70 so that the adsorbent surface of the TLC plate 80 is in contact with the top surface 74 of the strip 70. Pressure is then applied to the underside 76 of the depressions 72 forcing them to conform to the flat surface of the TLC plate 80 thus urging the sample towards the TLC plate 80. The displacement of the sample can be accomplished with a roller 78 as schematically shown in FIG. 9 or with an apparatus such as a flat plate (not shown), series of plungers (not shown), or the like.

Another alternative embodiment of the present invention is shown in FIGS. 12–17. A strip of FEP film 90 (preferably 0.025 mm in thickness) coated with perfluorokerosene or a similar perfluorinated fluid (not shown) is placed over a base plate 92 having a top 94 and at least one aperture 96 therein defining a cylinder. Slideably positioned within the cylinder 96 is a piston 98. The piston 98 has an aperture or outlet 100 along its central axis extending to a plenum 102 in communication with a source of suction (not shown) and a source of pressure (not shown). The piston 98 is comprised of an elongate upstanding portion 104 and an insert 106 preferably fashioned of a plastic material, such as a silicone polymer. The upstanding portion 104 has an enlarged diameter interior portion 108 to receive the insert 106 and a reduced diameter interior portion 110. The insert 106 has a central orifice 112 approximately 0.8 mm in diameter. The central orifice 112 in the insert is in fluid communication with the reduced diameter interior portion 110 of the piston and the plenum 102, both of which communicate with the source of suction and pressure.

With a top 114 of the piston or insert substantially flush with the top 94 of the base plate 92 as shown in FIG. 12, a vacuum may be applied to the orifice 112 of the insert which causes a small dimple 116 to form in the FEP film 90 overlaying the base plate and piston. It is found that a very well-defined dimple or hemispherical recess is formed in the FEP transfer sheet.

Figure 13:
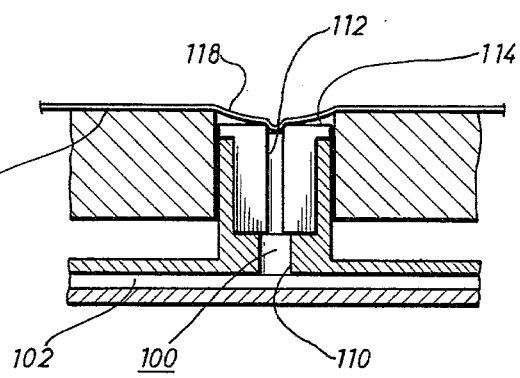
FIG. 13 is a partial-sectional view of the apparatus of the alternative embodiment of FIG. 12 and where a depression having a dimple has been formed in the applicator sheet.
Figure 14:
FIG. 14 schematically depicts a flexible applicator sheet in which a dimple has been formed with the apparatus in FIGS. 12 and 13.
Figure 15:
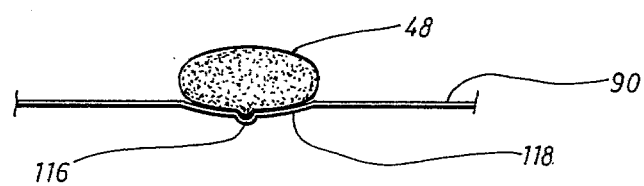
FIG. 15 schematically depicts the flexible applicator sheet of FIG. 14 which has been displaced by the apparatus of FIGS. 12 and 13 to form a depression therein and into which a sample has been introduced.
Figure 16:
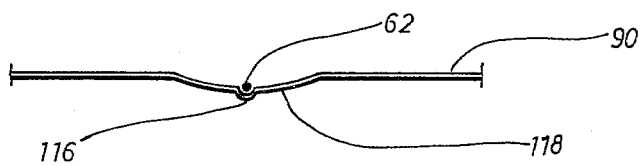
FIG. 16 schematically depicts the flexible applicator sheet of FIG. 15 after evaporation has taken place and showing the speck sample in the dimple.

The piston 98 is slideably displacable within the cylinder and may be moved downwardly as shown in FIG. 13 to position the top 114 of the piston slightly below the top 94 of the base plate 92. This results in there being formed in the transfer sheet a shallow depression 118 in which the small dimple is maintained. The dimple is maintained as a result of the suction, and the larger depression is formed as a result of the displacement of the piston downwardly which pulls on the transfer sheet or FEP film 90. It will, of course, be appreciated that the depression should be of a sufficient size to receive a test quantity of at least 50 microliters of sample solution.

Figure 17:
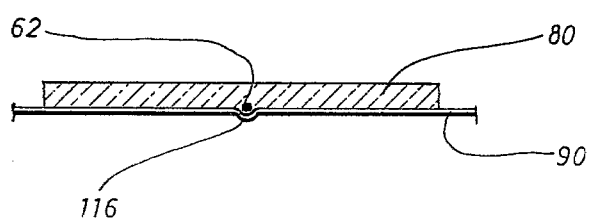
FIG. 17 schematically depicts a TLC plate overlying the apparatus of FIGS. 12 and 13 and wherein the sample is being urged into direct contact with the TLC plate.

As may be seen FIGS. 14–17, as the sample solution 48 is subjected to evaporation, the residue contained within it tends to accumulate within the central dimple. After evaporation is complete, a TLC plate 80 may be positioned over the transfer sheet 90 as shown in FIG. 17. The piston may be displaced upwardly to release the pull on the transfer sheet and slight pressure may be applied to the central orifice in the piston. Pressure on the dimple results in the sample being urged against the TLC plate 80 to effect a transfer of the sample thereonto.

EXAMPLE

A specific example of the method of the present invention would be as follows:
  (a) Polymer surface: FEP polymer
  (b) Solvent: chloroform
  (c) Solute: lipophilic dyes
  (d) Transfer fluid: perfluorokerene (PFK)

About 1% of the PFK is added to the chloroform solution of the dyes. A drop of sample thus prepared is introduced into a depression on the surface of the FEP polymer transfer sheet. As evaporation of the chloroform takes place on the transfer sheet surface, a film of PFK can be discerned under the droplet of dye solution. Continued evaporation of the solvent results in a single very small droplet of sample solution floating on the PFK film. Complete evaporation of the chloroform produces a tiny speck of solid sample which is readily transferred quantitatively to the TLC plate by direct contact of the absorptive layer of the plate to the FEP surface.

SUMMARY OF ADVANTAGES AND SCOPE OF THE INVENTION

It will be appreciated that in constructing an apparatus for preparing samples for application to a thin layer chromatographic plate according to the present invention, certain significant advantages are provided.

In particular, unlike the conventional means of introducing the sample to the TLC plates through single or repeated application of solutions followed by evaporation of the carrier solvent from the plate after each application, the present invention permits evaporation of the solvent prior to application. This results in an extremely small sample which may be applied very quickly to a TLC plate. In addition, a large number of samples may be applied simultaneously to a TLC plate by providing an apparatus having multiple control chambers or cuplike depressions. Moreover, there is avoided a sample having non-uniform density across its area as exists in the prior art. For example, samples in the prior art would leave a residue 52' (see FIG. 11) over a relatively large area and with concentric rings of zones of increased concentration of the sample.

The foregoing description of the invention has been directed to a particular preferred embodiment in accordance with the requirements of the patent statutes and for purposes of explanation and illustration. It will be apparent, however, to those skilled in this art that many modifications and changes in both apparatus and method may be made without departing from the scope and spirit of the invention. For example, it is within the contemplation of the present invention to provide a circular disc comprised of FEP polymer of, say, 20 mil. thickness which may be sequentially rotated over a block or base member having control chambers therein. With such an arrangement, a fully automated system may be provided to facilitate the application of many samples to a TLC plate moved into contact with the samples.

It will be further apparent that the apparatus of the present invention may be utilized, with suitable modifications within the state of the art, in a system which includes the sequenced introduction of TLC plates into a developing medium following the application of a speck sample.

These and other modifications of the invention will be apparent to those skilled in this art. It is the applicants' intention in the foregoing claims to cover all such equivalent modifications and variations as fall within the true spirit and scope of this invention.

What is claimed is:

1. Method for applying samples to a thin-layer chromatographic sheet comprising the steps of:
  providing a chemically inert, non-absorptive applicator plate;
  introducing a solution of a sample and a solvent into a depressed portion of the applicator plate;
  evaporating the solvent to provide a speck of sample on the transfer liquid; and
  transferring the speck to a thin-layer chromatographic sheet.

2. The method of claim 1 and further including a step of coating at least a portion of the applicator plate with a layer of transfer fluid prior to introduction of said sample and solvent.

3. The method of claim 1 and further including a step of forming said depression on a top surface of the applicator plate.

4. The method of claim 3 wherein said forming step comprises introducing a suction source at a location on a bottom surface of the applicator plate to displace a portion of the applicator plate adjacent the suction source towards the suction source.

5. The method of claim 3 wherein said forming step comprises molding a cup-like depression in the applicator plate.

6. The method of claim 2 wherein said coating step includes coating the applicator plate with a layer of polyfluorinated transfer fluid.

7. The method of claim 1 wherein said introducing step comprises forming said depression in the applicator plate and introducing the solution into the depression.

8. The method of claim 1 wherein said evaporating step comprises heating the applicator plate.

9. The method of claim 1 wherein said transferring step includes bringing the thin-layer chromotographic sheet into direct contact with the transfer fluid and the speck.

* * * * *